US012373917B1

(12) United States Patent
Frank

(10) Patent No.: US 12,373,917 B1
(45) Date of Patent: *Jul. 29, 2025

(54) DIGITAL TISSUE SEGMENTATION AND VIEWING

(71) Applicant: Steven Frank, Framingham, MA (US)

(72) Inventor: Steven Frank, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/618,252

(22) Filed: Mar. 27, 2024

Related U.S. Application Data

(63) Continuation of application No. 18/387,491, filed on Nov. 7, 2023, now Pat. No. 11,983,845, and a continuation-in-part of application No. 18/122,390, filed on Mar. 16, 2023, and a continuation-in-part of application No. 17/871,878, filed on Jul. 22, 2022, now Pat. No. 12,154,272.

(60) Provisional application No. 63/431,341, filed on Dec. 9, 2022.

(51) Int. Cl.
 *G06T 3/4053* (2024.01)
 *G06F 3/04845* (2022.01)
 *G06F 3/0488* (2022.01)
 *G06T 7/11* (2017.01)
 *G06T 11/00* (2006.01)
 *G06T 11/60* (2006.01)

(52) U.S. Cl.
 CPC ............. *G06T 3/4053* (2013.01); *G06T 7/11* (2017.01); *G06T 11/001* (2013.01); *G06T 11/60* (2013.01); *G06F 3/04845* (2013.01); *G06F 3/0488* (2013.01); *G06T 2200/24* (2013.01); *G06T 2207/10072* (2013.01); *G06T 2207/30004* (2013.01); *G06T 2210/41* (2013.01)

(58) Field of Classification Search
 CPC ....... G06T 3/4053; G06T 7/11; G06T 11/001; G06T 11/60; G06T 2200/24; G06T 2207/10072; G06T 2207/30004; G06T 2210/41; G06F 3/04845; G06F 3/0488
 See application file for complete search history.

(56) References Cited

U.S. PATENT DOCUMENTS

| | | | |
|---|---|---|---|
| 8,368,695 B2 | 2/2013 | Howell | |
| 8,849,308 B2 | 9/2014 | Marti | |
| 10,832,406 B2 | 11/2020 | Yu | |
| 11,195,060 B2 | 12/2021 | Frank | |
| 2016/0232703 A1* | 8/2016 | Duan | G06T 7/11 |
| 2021/0039828 A1 | 2/2021 | Song et al. | |
| 2023/0005016 A1 | 1/2023 | MacDonald-Korth et al. | |
| 2023/0334660 A1 | 10/2023 | Frank | |

FOREIGN PATENT DOCUMENTS

WO WO2015112263 7/2015

* cited by examiner

*Primary Examiner* — Yaron Cohen

(57) ABSTRACT

Methods and systems for representing a tissue segmentation from a source digital image computationally generate, from a source digital image of an anatomic region, a digital tissue segmentation visually indicating regions of interest corresponding to an abnormal condition associated with at least portions of the anatomic region. The source image and the tissue segmentation may be alternately displayed in registration on a mobile device at a gesturally selected magnification level.

20 Claims, 4 Drawing Sheets

DIGITAL TISSUE SEGMENTATION AND VIEWING

CROSS-REFERENCE TO RELATED APPLICATION

This application is a continuation of U.S. Ser. No. 18/387,491, filed on Nov. 7, 2023, which is a continuation-in-part of U.S. Ser. No. 18/122,390, filed on Mar. 16, 2023 and Ser. No. 17/871,878, filed on Jul. 22, 2022, and also claims priority to, and the benefit of, U.S. Provisional Patent Application No. 63/431,341 (filed on Dec. 9, 2022). These priority documents are hereby incorporated by reference in their entireties.

FIELD OF THE INVENTION

The present invention relates, generally, to processing and automated classification of large, high-resolution digital images, and in particular to visually representing classification results corresponding to different tissue types and/or subtypes.

BACKGROUND

"Deep learning" approaches have been applied to a wide range of medical images with the objective of improving diagnostic accuracy and clinical practice. Many efforts have focused on images that are inherently small enough to be processed by convolutional neural networks (CNNs), or which can be downsampled to a suitable size without loss of fine features necessary to the classification task. Commonly used CNNs running on standard hardware can comfortably handle image dimensions ranging from 100×100 pixels to 600×600 pixels; larger images entail complex architectures that are difficult to train, perform slowly, and require significant memory resources. Among the most challenging medical images to analyze conputationally are digital whole-slide histopathology images, which are often quite large—10,000 to more than 100,000 pixels in each dimension. Their large size means that even traditional visual inspection by trained clincians is difficult. To make such images amenable to CNN analysis, researchers have decomposed them into much smaller tiles that are processed individually. A probability framework may be applied to the tile-level classifications to classify the slide (see, e.g., U.S. Pat. No. 10,832,406). The most successful recent studies have achieved performance comparable to that of experienced specialists.

A longstanding impediment to clinical adoption of machine-learning techniques is the inability of many such techniques to convey the rationale behind a classification, diagnosis or other output. Black-box models whose reasoning is opaque or impervious to retrospective analysis may pose clinical dangers that outweigh the benefits of a computational approach. Until recently, CNNs have fallen squarely within the black-box category, but techniques such as gradient-based class saliency maps and gradient-weighted class activation maps ("Grad-CAM") have pried the box open, highlighting the image regions important to a CNN classification.

More generally, the ability to visualize distinct tissue regions in a medical image can be important diagnostically whether or not an explicit classification is involved. Computational techniques for automatic "tissue segmentation" partition an image into segments corresponding to different tissue classes, e.g., whole organs or organ sub-regions (such as liver or lung segments, or muscle groups). Areas with pathologies such as tumors or inflammation can also be isolated using segmentation. Traditionally, diagnoses have been based on manual measurement of lesion dimensions and their number in a medical image. More recently, the role of imaging has grown beyond diagnosis to include quantitative characterization of tissue volume or shape, chemical composition, and functional activity; automated tissue segmentation has played an important part in this evolution. But segmentation techniques tend to be complex and computationally demanding, and may require knowledge of the imaged anatomical structure or other a priori information.

One consequence of this is the cumbersome manner in which segmentations are presented visually. Anatomic features corresponding to disease states or subtypes may be quite small, necessitating the ability to study the regions of interest (ROIs) in an image at high magnification; this, in turn, typically implies the need to buffer the entire image which, in the case of a histopathology slide, can be quite large. A ROI may be circled or otherwise identified in the image, and the user magnifies and inspects the region using a peripheral device such as a mouse or touchpad. Virtually all analytical tools involving ROI prediction involve some tradeoff between sensitivity (correctly identifying diseased regions) and precision or specificity (correctly excluding non-diseased tissue). For safety, medical image analysis typically emphasizes sensitivity in order to avoid missing disease. The price, of course, is visual "false alarms" that distract attention from the diseased tissue regions and reduce the usefulness of the analysis tool.

SUMMARY

Embodiments of the present invention facilitate review of scaled-down images large enough to reveal anatomic features relevant to a condition under study but, often, much smaller than a source image. ROIs may be visually indicated, e.g., marked in colors corresponding to probability levels or bins associated with a disease condition, thereby enabling clinicians to focus attention progressively on different areas of the image to avoid fatigue and distraction (and mitigating the "false alarm" problem). For visual clarity, color may translucently overlie a grayscale version of the image. In some embodiments, the user may toggle between the source image and the colored ROI map. When deployed on a touchscreen device, the invention may enable users to gesturally control image magnification (e.g., using pinch and stretch gestures) and toggle between substantially identically magnified, registered versions of the source image and the colored ROI map.

Embodiments of the invention may deployed on mobile devices. By "mobile device" is meant portable, typically hand-held electronic devices that can connect to the internet and typically include touchscreen capability. These include "smart phones" (such as the iPHONE sold by Apple Inc. and various phones running the ANDROID operating system supported by Google LLC) and tablet computers (e.g., the iPAD marketed by Apple Inc.). Laptop computers with touchscreens may be considered mobile devices. Common among them is the ability of users to gesturally manipulate displayed images, including altering the magnification thereof.

Embodiments of the invention can provide accurate tissue segmentations that do not require a priori knowledge of tissue type or other extrinsic information not found within the subject image. Moreover, the approaches discussed herein may be combined with classification analysis so that diseased tissue is not only delineated within an image but also characterized in terms of disease type. The techniques may be applied even to very large medical images such as digital pathology slides. In various embodiments, a source image is decomposed into smaller (e.g., overlapping) subimages such as square or rectangular tiles, which may, in some cases, be sifted based on a visual criterion. The visual criterion may be one or more of image entropy, density, background percentage, or other discriminator. A CNN produces tile-level classifications that are aggregated to produce a tissue segmentation and, in some embodiments, to classify the source image or a subregion thereof.

Overlapping subimages represents a useful data-augmentation expedient for training purposes, but also is found to enhance classification of test images and mapping accuracy, with the enhancement depending directly on the degree of overlap. In particular, the greater the degree of overlap, the greater will be the number of images that may contribute to the classification of any particular pixel, thereby potentially increasing the accuracy of the tissue segmentation.

In some implementations, a mobile device is configured to represent a tissue segmentation from a source digital image. The mobile device may comprise a processor; a computer memory including a first memory partition image buffer for storing a source digital image of an anatomic region (e.g., an in vivo region in an X-ray or mammogram or an in vitro tissue sample such as a biopsy or resection) and a second memory partition for storing a tissue segmentation image digitally indicating probabilities of an abnormal condition associated with at least portions of the anatomic region (where the probabilities may, if desired, be indicated by at least two different colors); and a touchscreen in operative communication with the processor for (a) displaying a first one of the source digital image or the tissue segmentation image, (b) receiving a gestural command and, in response, changing the magnification of the displayed first image, and (c) in response to a toggle command, displaying the other image at a substantially identical magnification level and in registration with the first image (i.e., congruent in the same coordinate system). The processing of the source image and assembly of the tissue segmentation image may occur on the mobile device or remotely, at a server; in the latter case, the server may transmit the tissue segmentation image (or portion thereof) to the mobile device for display thereon along with the source image, facilitating the toggling operation.

The memory partition may be an image buffer or, in the case where rendering instructions rather than image data is stored, a register or location in volatile memory. If the tissue segmentation is an overlay on the source image, displaying the tissue segmentation can mean applying the overlay to the source image, and displaying the source image can correspond to removing the overlay therefrom. In some cases, the critical anatomy facilitating proper segmentation may be too small, and the analyzed image therefore too large, for practical transmission to and from (and viewing on) the mobile device. In such cases, the server may generate the segmentation based on one or more higher-resolution versions of the source image, but may transmit a scaled-down version of the tissue segmentation image (and a scaled-down version of the source image if one is not already stored locally) to the mobile device. In such cases, the resolution of the scaled-down image may be insufficient for clinical use, i.e., a medical practitioner may wish to view the critical anatomy at a higher resolution. In such cases, the server may store a mapping between the higher-resolution and scaled-down versions of the image. When the user of the mobile device enlarges the local, scaled-down image, coordinates specifying the displayed portion are sent—either upon user command or automatically by the mobile device—to the server, which fetches that portion of the source image or tissue segmentation image based on the stored mapping. The retrieved image portion at higher resolution is sent to the mobile device, which uses it to overwrite the currently displayed lower-resolution image portion. It should be emphasized that the viewing application may be local to the mobile device or may be a web application hosted on a server and delivered over the internet through a browser interface. In such cases the currently viewed image resides in a display buffer and the other image is either cached locally or, in some cases, maintained at the server until the user switches images, at which point it is retrieved. The distribution of storage and functionality between the local device and the server in a web-application implementation may be straightforwardly achieved based on considerations of performance and convenience.

Accordingly, in a first aspect, the invention pertains to a method of computationally representing a tissue segmentation image from a source digital image. In various embodiments, the method comprises the steps of, at a remote computer, computationally generating, from a source digital image of an anatomic region, a digital tissue segmentation image visually indicating regions of interest corresponding to a physiologic condition associated with at least portions of the anatomic region; storing, at a server, at least one lower-resolution version of the source image; and on a mobile device, (i) alternately displaying each of the source image and the tissue segmentation image in registration at a gesturally selected magnification level and at a first resolution level, and (ii) replacing the displayed source image with a corresponding portion of a higher-resolution version thereof obtained from the server. Of course, the server where the the tissue segmentation is generated need not be the same server that communicates with the local device. As used herein, the expression "a server" is used for convenience to connote a single server or multiple servers. Moreover, the terms "at a server" and "at the server" connotes an operation that occurs on the physical server device or on a different device accessible to the server.

The remote computer is distinct from a user's mobile device; it may be a server (possibly, but not necessarily, the server in communication with the mobile device), a high-performance computer in communication with a webserver that itself communicates with user mobile devices, or other device. For example, the user may upload a source image for analysis and segmentation using an application programming interface (API), an upload page, or other communication modality. Typically the uploaded image is received by a server that supports the upload functionality. The image may be analyzed by the server itself if the server implements the analysis and segmentation functionality described herein, or the server may communicate the image to another computational device (a GPU-enabled workstation or other stand-alone computer, another server, etc.) for analysis. The segmentation is communicated to the mobile device by a server, typically a webserver, which may be the same server that received the uploaded image or it may be a different server. Accordingly, the functions of obtaining source images, computationally generating digital tissue segmentations based thereon, and serving the analyzed images to user mobile devices may be performed by a single computational device or a plurality of computational devices.

In various embodiments, the method further comprises receiving, at the server, coordinates from the mobile device specifying a displayed portion of the source image or the tissue segmentation image and responsively making a corresponding portion of the higher-resolution source image available to the mobile device. For example, a plurality of higher-resolution images may each be represented at the server by a plurality of tiles having a tile count determined by an image resolution, where the corresponding portion of the higher-resolution source image obtained from the server comprises or consists of tiles. Alternatively, a plurality of higher-resolution source images may each be represented at the server as unitary images, where the corresponding portion of the higher-resolution image obtained from the server comprises, consists of or is a single image. For example, the plurality of higher-resolution source images may be related to each other by at least one geometric transformation.

In various embodiments the method further comprises, at the server, computationally generating the digital tissue segmentation from the source digital image at a selected one of the plurality of resolutions; applying the digital tissue segmentation to the source image at other resolutions; and responsive to an increase in magnification of a displayed digital tissue segmentation on the mobile device, replacing the displayed digital tissue segmentation with corresponding subject matter from a higher-resolution representation thereof. The digital tissue segmentation may include a plurality of overlays designating, and colorwise distinguishing, high-precision regions of interest and high-recall regions of interest superimposed on corresponding regions of the digital source image. The regions may be overlaid as outline regions or boxes or as filled regions or boxes.

In some embodiments, the method further comprises computationally analyzing one or more of the regions of interest to identify a subtype associated therewith. The subtype may be, for example, a cancer subtype or a cancer severity level.

Another aspect of the invention relates to a system comprising, in various embodiments, a remote computer configured to computationally generate, from a source digital image of an anatomic region, a digital tissue segmentation image visually indicating regions of interest corresponding to a physiologic (e.g., abnormal or disease) condition associated with at least portions of the anatomic region; a server; a storage device for storing, accessibly to the server, at least one lower-resolution version of the source image; and a mobile device configured to (i) alternately display each of the source image and the tissue segmentation image in registration at a gesturally selected magnification level and at a first resolution level, and (ii) replace the displayed source image with a corresponding portion of a higher-resolution version thereof obtained from the server. The remote computer is remote in the sense that it is physically distinct from the mobile device. It may be the same device as the recited server or it may be a different device, e.g., in communication with the server. Similarly, the storage device may be physically associated with or part of the server, or may be separate but accessible to the server.

In various embodiments, the server and the remote computer are further configured to computationally generate the digital tissue segmentation from the source digital image at a selected one of the plurality of resolutions; apply the digital tissue segmentation to the source image at other resolutions; and responsive to an increase in magnification of a displayed digital tissue segmentation on the mobile device, cause the displayed digital tissue segmentation to be replaced with corresponding subject matter from a higher-resolution representation thereof.

In still another aspect, the invention relates to a mobile device configured to represent a tissue segmentation from a source digital image. In various embodiments, the mobile device comprises a processor; a computer memory comprising a first memory partition for storing a source digital image of an anatomic region and a second memory partition for storing a digital tissue segmentation image visually indicating regions of interest corresponding to an abnormal condition associated with at least portions of the anatomic region; and a touchscreen in operative communication with the processor for (a) displaying a first one of the source digital image or the tissue segmentation image, (b) receiving a gestural command and, in response, increasing a magnification of the displayed first image and sending, to a server, data indicative of the increased magnification, (c) receiving, from the server, a higher-resolution version of the first image as currently displayed on the touchscreen, and (d) replacing, on the touchscreen, the first image as currently displayed with the received higher-resolution version.

In some embodiments, the corresponding portion of the higher-resolution image obtained from the server is a single image. Alternatively, the corresponding portion of the higher-resolution image obtained from the server may be a plurality of image tiles. The digital tissue segmentation may include a plurality of overlays designating, and colorwise distinguishing, high-precision regions of interest and high-recall regions of interest superimposed on corresponding regions of the digital source image. For example, the digital tissue segmentation may colorwise distinguish a plurality of subtypes of the abnormal condition. In various embodiments, the tissue segmentation image is a 3D tomographic reconstruction of an anatomic region.

The processor may be configured to alternately display the second one of the source digital image or the tissue segmentation image in registration with the first one of the source digital image or the tissue segmentation image at the increased magnification. The computer memory may be configured to store a plurality of source digital images and corresponding segmentation images, where the plurality of source and corresponding segmentation images are presented on the touchscreen in a ranked order indicating priorities thereamong based at least in part on the regions of interest.

In another aspect, the invention relates to a method of computationally representing a tissue segmentation from a source digital image. In various embodiments, the method comprises the steps of computationally generating, from a source digital image of an anatomic region, a digital tissue segmentation visually indicating regions of interest corresponding to an abnormal condition associated with at least portions of the anatomic region; and alternately displaying the source image and the tissue segmentation in registration on a mobile device at a gesturally selected magnification level.

In various embodiments, the method further comprises representing the source digital image at a plurality of resolutions; relating the representations of the source image at the different resolutions via at least one geometric transformation; and responsive to an increase in magnification of a displayed image on the mobile device, replacing the displayed image with corresponding subject matter from a higher-resolution representation thereof.

The method may further comprise the steps of computationally generating the digital tissue segmentation from the source digital image at a selected one of the plurality of resolutions; applying the digital tissue segmentation to the source image at other resolutions; and responsive to an increase in magnification of a displayed digital tissue segmentation on the mobile device, replacing the displayed digital tissue segmentation with corresponding subject matter from a higher-resolution representation thereof.

In some embodiments, the source image is stored at multiple resolutions at a server in communication with the mobile device; the server may be configured to select the higher-resolution source image based on the increased magnification and to communicate a portion of the higher-resolution image to the mobile device for display thereon. The tissue segmentation may be generated remotely (e.g., at the server) and communicated to the mobile device for display, alternately with the source image, thereon. In other embodiments, the source image is stored at multiple resolutions on the mobile device, which is configured to replace the displayed image with a higher-resolution version of the displayed subject matter obtained from a higher-resolution source image.

In various embodiments, the digital tissue segmentation includes a plurality of color overlays or outlines each associated with a probability range for the abnormal condition and superimposed on corresponding regions of the digital image. The colors may, for example, be translucently superimposed over a grayscale version of the source image, or may instead surround the regions as outline borders (which may be colored). Each highlighted region may correspond to a union of overlapping subimage regions of the source image that have been individually analyzed and assigned classification probabilities by a neural network. Classification probabilities for overlapping subimage regions may be combined at a pixel level. The classification probabilities for pixels of the overlapping subimage regions may correspond to a maximum, a minimum or an average (which may be weighted or unweighted) of the probability values assigned to overlapping subimage region. Overlapping subimage regions may be obtained, for example, by selecting, from a candidate set of subimage regions, the subimage regions having image entropies between a pair of boundary entropy values Alternatively or in addition, the digital tissue segmentation may include a plurality of overlays designating, and colorwise distinguishing, high-precision regions of interest and high-recall regions of interest superimposed on corresponding regions of the digital image. The method may, in some embodiments, include the step of computationally analyzing one or more regions of interest to identify a classification subtype associated therewith. In various embodiments, the source image is a downscaled version of a larger image obtained using an imaging modality; the source image is sufficiently large to reveal anatomic features associated with the abnormal condition.

In another aspect, the invention pertains to a mobile device configured to represent a tissue segmentation from a source digital image. In various embodiments, the mobile device comprises a processor; a computer memory comprising a first image buffer for storing a source digital image of an anatomic region and a second image buffer for storing a digital tissue segmentation image visually indicating regions of interest corresponding to an abnormal condition associated with at least portions of the anatomic region; and a touchscreen in operative communication with the processor for (a) displaying a first one of the source digital image or the tissue segmentation image, (b) receiving a gestural command and, in response, changing a magnification of the displayed first image, and (c) in response to a toggle command, displaying the other image at a substantially identical magnification level and in registration with the first image.

In some embodiments, the processor is configured to generate the tissue segmentation, whereas in other embodiments, the tissue segmentation is generated remotely and the processor is configured to receive the tissue segmentation and cause display thereof on the mobile device. The digital image may be represented at a plurality of resolutions related to each other via at least one geometric transformation. The processor may be configured to sense an increase in magnification of a displayed image on the mobile device and, in response thereto, to obtain and replace the displayed image with corresponding subject matter from a higher-resolution representation thereof.

In various embodiments, the processor is further configured to respond to an increase in magnification of a displayed digital tissue segmentation by replacing the displayed digital tissue segmentation with corresponding subject matter from a higher-resolution representation thereof.

The digital tissue segmentation may include a plurality of color overlays or outlines each associated with a probability range for the abnormal condition and superimposed on corresponding regions of the digital image. Alternatively or in addition, the digital tissue segmentation may include a plurality of overlays or outlines designating, and colorwise distinguishing, high-precision regions of interest and high-recall regions of interest superimposed on corresponding regions of the digital image.

In yet another aspect, the invention relates to a server for interacting with a mobile device and handling images for display thereon. In various embodiments, the server comprises a processor and a computer memory for storing a high-resolution image of an anatomic region and a mapping between the high-resolution image and a lower-resolution image of the anatomic region. The processor is configured to receive data specifying a portion of the lower-resolution image and, in response, to retrieve a corresponding portion of the high-resolution image and make the corresponding portion available to another device for display thereon. The other device may be, for example, a mobile device and the processor may retrieve and make the corresponding portion available in response to a command issued by the mobile device.

In various embodiments, the processor is further configured to generate, from the high-resolution image, a digital tissue segmentation visually indicating regions of interest corresponding to an abnormal condition associated with at least portions of the anatomic region, and to transmit the tissue segmentation image to another device at a lower resolution.

In some embodiments, the processor is further configured to computationally analyze one or more regions of interest to identify a classification subtype associated therewith.

In some embodiments, the server is configured to generate the tissue segmentation image using a convolutional neural network, an object detector, or both. Coordinates of the image displayed on the mobile device may be received at the server without action by a user of the mobile device, or may be received at the server upon action taken on the mobile device (e.g., tapping a touchscreen icon, label or image feature) by a user thereof.

Yet another aspect of the invention relates to a method of computationally generating a tissue segmentation from a digital image of an anatomic region. In various embodiments, the method comprises the steps of computationally generating a plurality of overlapping subimage regions of the digital image; computationally sifting the subimage regions in accordance with a visual criterion; computationally generating classification probabilities for the sifted subimage regions, the classification probabilities corresponding to first and second tissue types; computationally generating the tissue segmentation from subimage regions whose classification probabilities specify a first of the at least two tissue types; and further computationally analyzing the subimage regions whose classification probabilities specify the first tissue type to generate classification probabilities corresponding to subtypes of the first tissue type.

In still another aspect, the invention pertains to an image-processing system for computationally generating a tissue segmentation from a source digital image of an anatomic region. In various embodiments, the system comprises a processor; a computer memory; a first image buffer for storing a source image; a tiling module for computationally generating a plurality of overlapping subimage regions of the source digital image; a subimage analyzer for computationally sifting the subimage regions in accordance with a visual criterion; a first classifier, executed by the processor, for computationally generating classification probabilities for the sifted subimages, the classification probabilities corresponding to first and second tissue types; a mapping module for computationally generating the tissue segmentation from subimage regions whose classification probabilities specify a first of the at least two tissue types; and a second classifier, executed by the processor, for computationally analyzing the subimage regions whose classification probabilities specify the first tissue type to generate classification probabilities corresponding to subtypes of the first tissue type.

As used herein, the term "substantially" or "approximately" means±10%, and in some embodiments, 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

DESCRIPTION OF THE DRAWINGS

The foregoing discussion will be understood more readily from the following detailed description of the disclosed technology, when taken in conjunction with the following drawings, in which.

DESCRIPTION

Figure 1:
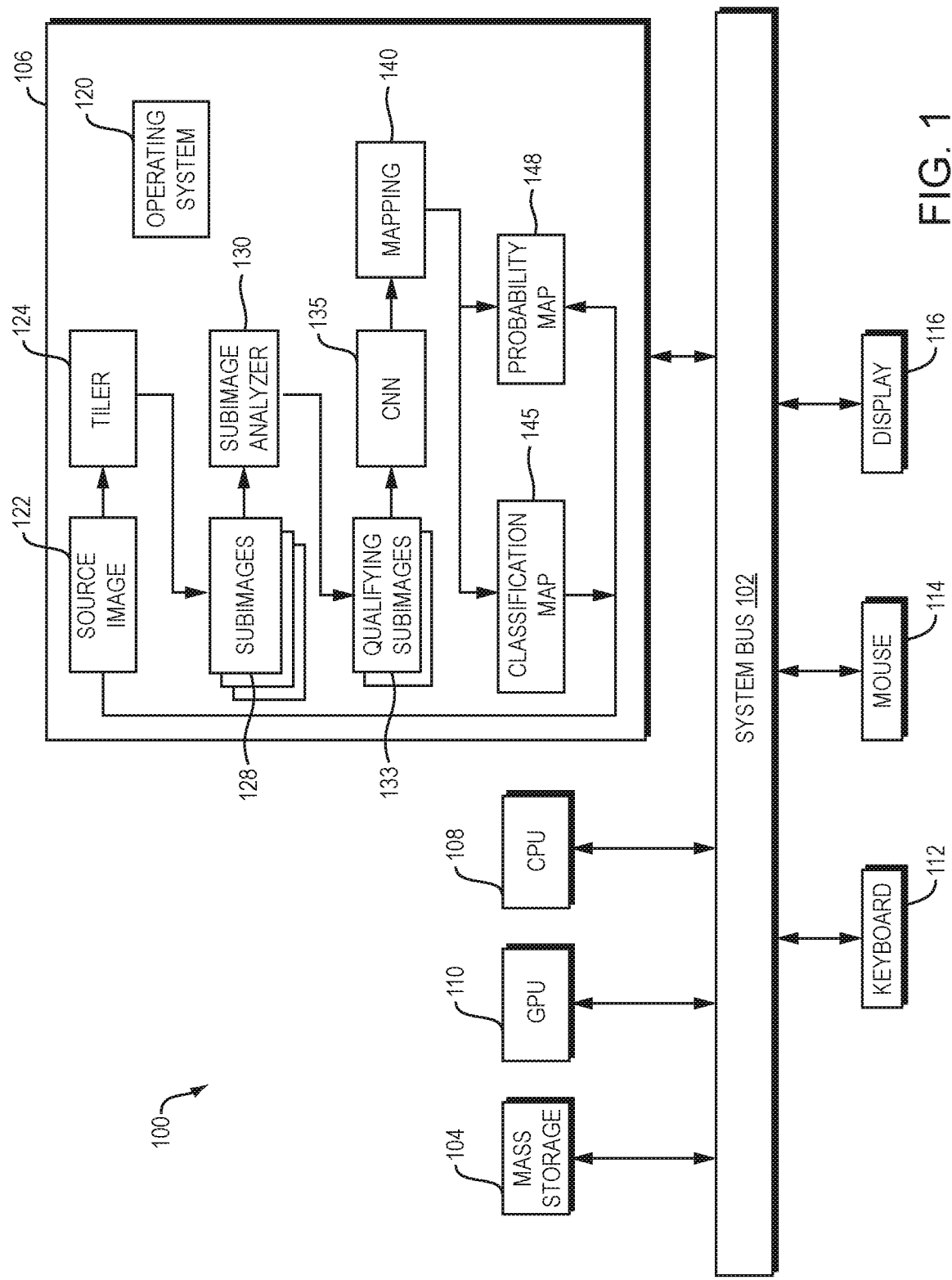
FIG. 1 schematically illustrates a representative hardware architecture according to embodiments of the invention.

Refer first to FIG. 1, which illustrates a representative system 100 implementing an embodiment of the present invention; the system 100 may be a computer such as a server, as discussed below, but may instead be a mobile device or other computational device (e.g., in communication with a server). As indicated, the system 100 includes a main bidirectional bus 102, over which all system components communicate. The main sequence of instructions effectuating the functions of the invention and facilitating interaction between the user and the system reside on a mass storage device (such as a hard disk, solid-state drive or optical storage unit) 104 as well as in a main system memory 106 during operation. Execution of these instructions and effectuation of the functions of the invention are accomplished by a central processing unit ("CPU") 108 and, optionally, a graphics processing unit ("GPU") 110. The user interacts with the system using a keyboard 112 and a position-sensing device (e.g., a mouse) 114. The output of either device can be used to designate information or select particular areas of a screen display 116 to direct functions to be performed by the system. Alternatively, the screen display 116 may be a touchscreen.

The main memory 106 contains instructions, conceptually illustrated as a group of modules, that control the operation of CPU 108 and its interaction with the other hardware components. An operating system 120 directs the execution of low-level, basic system functions such as memory allocation, file management and operation of mass storage devices 104. At a higher level, a source image 122, stored (e.g., as a NumPy array) in an image buffer that may be a partition of main memory 106, may be processed by a tiler module 124 to produce a plurality of subimage portions (or "tiles") 128 of source image 122 based on a user-specified or default overlap factor. Tiles 128 may be stored in a storage device 104 along with coordinates specifying their locations in source image 122.

In some embodiments, an analyzer 130 sifts subimages 128 according to a visual criterion, as described in greater detail below, to identify the subimages 133 that satisfy the criterion. The qualifying subimages 133 are analyzed by a CNN 135 (or other classifier, such as an attention network) that has been trained for the classification task of interest. CNN 135 may be straightforwardly implemented without undue experimentation. Python/Keras code for a suitable five-layer CNN architecture may be found at https://github.com/stevenjayfrank/A-Eye, the contents of which are incorporated by reference herein. In embodiments that do not implement sifting, all subimages are treated as qualifying.

CNN 135 computes a classification probability for each qualifying subimage 133. A mapping module 140 builds a classification map 145 by computing the average probability associated with each classified pixel across all subimages that include that pixel, or otherwise combining pixel-level probabilities as described below. From classification map 145, mapping module 140 generates the probability map 148 based on the final probability value of each classified pixel and the color associated with that value. Because only part of the original source image may have associated probability levels (since, usually, not all subimages satisfy the visual criterion), it may be useful for probability map 148 to represent source image 122 as a grayscale (or line or other monochromatic) image with colors overlaid translucently where probabilities were obtained. Alternatively, identified regions may be outlined in, rather than filled with, a color indicative of the probability level. In still other embodiments, the probability map consists primarily or entirely of the colored regions on a monochromatic (e.g., white) background. This is useful for detection of conditions such as perineural invasion, where the feature size (in this case nerve tissue) can be quite small and would be difficult to discern against a grayscale image. These and other alternatives are straightforwardly implemented in accordance with well-known techniques, and are collectively referred to as "overlays."

Classification map 145 and probability map 148 may be stored in memory 106 as data arrays, image files, or other data structure, but need not be distinct. Instead, probability map 148 may be generated directly from the source image (e.g., in grayscale format) and average (or otherwise combined) pixel-level classification probabilities as these are computed—i.e., the probability and classification maps may be the same map.

In one embodiment, tiler 124 generates subimage tiles 128 of specified dimensions from a source image 122 by successive identification of vertically and horizontally overlapping tile-size image regions. The Python Imaging Library, for example, uses a Cartesian pixel coordinate system, with (0,0) in the upper left corner. Rectangles are represented as 4-tuples, with the upper left corner given first; for example, a rectangle covering all of an 800×600 pixel image is written as (0, 0, 800, 600). The boundaries of a subimage of width=w and height=h are represented by the tuple (x, y, x+w, y+h), so that x+w and y+h designate the bottom right coordinate of the subimage.

Figure 2:
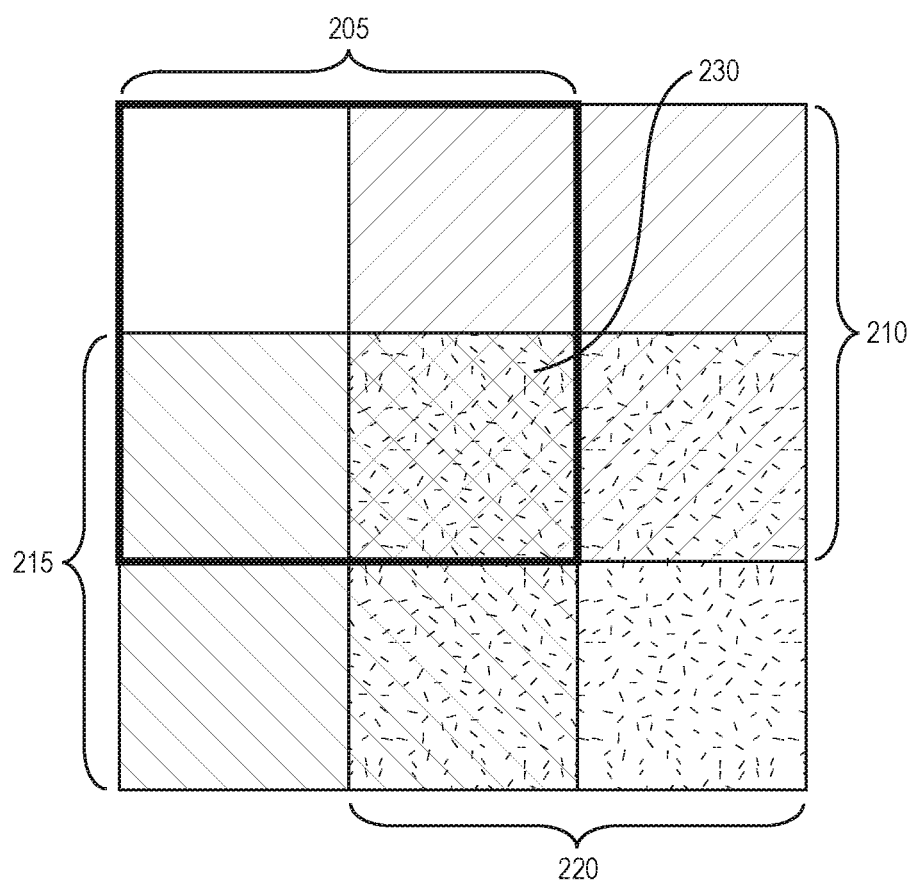
FIG. 2 illustrates two-dimensional overlap among subimages.

The tile overlap factor may be defined in terms of the amount of allowed overlap between vertically or horizontally successive subimages; hence, an overlap factor of ½ results in 50% vertical or horizontal overlap between consecutive subimages. This is illustrated in FIG. 2. Tile pairs 205, 210 and 215, 220 have 50% horizontal overlap (with the border of tile 205 being emphasized for clarity). In addition, tile pair 215, 220 has 50% vertical overlap with tile pair 205, 210. This two-dimensional overlap results in a central region 230 where all four tiles 205, 210, 215, 220 overlap and may contribute, by averaging or other combination, to a classification probability. The greatest number of overlapping images occupy the central region 230, which, as overlap increases, diminishes in size but increases in terms of the number of contributing subimages. More importantly, increasing overlap means that more of the area of any single tile will overlap with one or more other tiles, so that more pixels of any tile will receive probability contributions from other tiles with consequent reduction in classification error; consequently, if only a minority of tiles are misclassified, the effect of overlap by properly classified tiles will overwhelm the misclassification error and the resulting probability map will have high accuracy. Typical overlap factors exceed 50%, e.g., 60%, 70%, 80%, or even 90% or more along both dimensions.

Once the tiles are generated, they may be sifted in accordance with a visual criterion with the objective of eliminating tiles that are not meaningful for classification. In one embodiment, the visual criterion is image entropy. From the purview of information theory, image entropy represents the degree of randomness (and therefore information content) of the image pixel values, just as the entropy of a message denotes (as a base-2 log) the amount of useful, nonredundant information that the message encodes:

$$H = -\sum_{k} p_k \log_2(p_k)$$

In a message, $p_k$ is the probability associated with each possible data value k. For an image, local entropy is related to the complexity within a given neighborhood, sometimes defined by a structuring element such as a circular or square region, or the entire image. Thus, the entropy of a grayscale image (or one channel of a color (e.g., RGB) image) can be calculated at each pixel position (i,j) across the image. To the extent that increasing image entropy correlates with increasingly rich feature content captured in the convolutional layers of a CNN, it provides a useful basis for selecting tiles. In one implementation, only those tiles whose entropies equal or exceed the entropy of the whole image are retained. Although no subimage will contain as much information content as the original, a subimage with comparable information diversity may pack a similar convolutional punch, so to speak, when processed by a CNN. In some embodiments, depending on the distribution of tile entropies, the discrimination criterion may be relaxed in order to increase the number of qualifying tiles. Because of the logarithmic character of the entropy function, even a slight relaxation of the criterion can result in many more qualifying tiles. For example, the criterion may be relaxed by 1% (to retain tiles with image entropies equal to or exceeding 99% of the source image entropy), or 2%, or 3%, or 4%, or 5%, or up to 10%. Tile sifting using image entropy is further described in Frank et al., "Salient Slices: Improved Neural Network Training and Performance with Image Entropy," *Neural Computation*, 32(6), 1222-1237 (2020), which is incorporated by reference herein.

Another suitable approach to tile sifting uses a background threshold criterion, retaining only tiles with a proportion of background below a predetermined limit. Images of pathology slides, for example, typically have white or near-white backgrounds. But the tissue of interest may also have white features, gaps or inclusions. Hence, while the presence of any background can adversely affect training and classification accuracy, eliminating all tiles containing regions that might potentially be background risks discarding anatomy critical to classification. As a result, the minimum background threshold is generally set at 50% or higher, e.g., 60%, 70%, 80%, or even 90%; the optimal threshold depends on the amount of background-shaded area that may appear in non-background regions.

One approach to background identification and thresholding is to convert a colored tile to grayscale and count pixels with color values corresponding to background, e.g., white or near-white pixels. For example, an RGB image has three color channels and, hence, three two-dimensional pixel layers corresponding to red, blue, and green image components. In an eight-bit grayscale image, a pixel value of 255 represents white. To allow for some tonal variation from pure white arising from, for example, the source imaging modality, any pixel in any layer with a value above, e.g., 240 may be considered background. Summing the number of such pixels and dividing by the total number of pixels yields the background fraction. Only tiles with background fractions below the predetermined threshold are retained.

Still another suitable visual criterion is image density. If regions of interest for classification purposes are known to have image densities above a minimum, that minimum may be used as a discrimination threshold to sift tiles. See, e.g., the '406 patent mentioned above.

With renewed reference to FIG. 1, once qualifying tiles 133 identified and stored in volatile and/or nonvolatile storage, they are used either to train CNN 135 or are presented to a trained CNN as candidate images for classification. The output of CNN 135 is generally a classification probability. In some instances, the classification is binary (e.g., cancerous or benign, adenocarcinoma or squamous cell carcinoma, etc.) and the decision boundary lies at, e.g., 0.5, so that output probabilities at or above 0.5 correspond to one classification and output probabilities below 0.5 reflect the other classification. In other instances, there are multiple output classifications and a "softmax" activation function maps CNN output probabilities to one of the classes.

For ease of illustration, consider binary classification of a histology slide that may contain either or both of two types—"type 1" and "type 2"—of cancerous tissue. The slide, possibly after initial resizing (e.g., downsampling to a lower resolution), is decomposed into overlapping subimages 133, which are sifted as described above. The sifted subimages are processed by CNN 135, which has been trained to distinguish between type 1 and type 2 cancers. CNN 135 assigns a classification probability p to each subimage, with probabilities in the range $0.5 \leq p < 1.0$ corresponding to type 1 and probabilities in the range $0 < p < 0.5$ corresponding to type 2 (assuming a decision boundary at 0.5). Each individual subimage may contain only a small amount of type 1 or type 2 tissue, yet the entire subimage receives a unitary probability score. As a result, the score assigned to an individual subimage may be skewed so as, for example, to ignore type 1 and/or type 2 tissue that is present but in too small a proportion to trigger the proper classification. With sufficient overlap and pixel-level averaging, this classification error will be mitigated as overlapping subimages containing progressively greater proportions of the type 1 and/or type 2 tissue contribute to the average pixel-level probabilities.

In various embodiments, a pixel-level probability map is defined to reflect average probabilities across all classified subimages. For example, in Python, a 3D $m \times n \times d$ NumPy array of floats may be defined for an $m \times n$ source image, with the parameter d corresponding to the number of classified subimages (which were identified as satisfying a visual criterion). At each level d, the array is undefined or zero except for the region corresponding to one of the classified subimages, and all array values in that 2D region are set to the classification probability computed for the subimage. The probability map is an $m \times n$ array, each value [i,j] of which is equal to some combination of all nonzero values [i,j,d:] of the 3D array, e.g., the average of all nonzero values [i,j] over the d-indexed axis. The greater the degree of subimage overlap, the deeper the number of nonzero values will extend through the d-indexed axis and, therefore, the more probability values (from overlapping subimages) that will contribute to the combined value at any point of the probability map, enhancing classification accuracy for that point. Points in the probability map corresponding to points in the 3D array with no nonzero values over the d-indexed axis—i.e., where the source image lacked sufficient image entropy to generate a subimage satisfying the criterion—may be left undefined. The probability map, therefore, is a map of pixelwise classification probabilities. The probability map may be dense (i.e., have values over most of the source image) or sparse (with relatively few defined values) depending on the amount of visual diversity in the source image and the number of qualifying tiles left after sifting.

In another approach, which may be applied in addition to or instead of the tile-based approach noted above, an object detector may be used to find image features corresponding to tissue abnormalities. This approach is useful if the source image is relatively small and/or downscaling does not materially affect the ability of the object detector to identify ROIs. For example, an object detector may accept as input the entire source image 122, a rescaled version thereof or a portion thereof. Suitable object-detection systems include RCNN, Fast RCNN, Faster RCNN, Mask RCNN, pyramid networks, EfficientDet, DETR, and YOLO (e.g., any of YOLO versions v1-v8). Object-detection algorithms may predict the dimensions and locations of bounding boxes surrounding objects that the algorithm has been trained to recognize (although some, like Mask RCNN, predict object contours). Bounding boxes or contours having probability scores below a threshold may be dropped. For example, the object detector may be used to identify abnormal tissue regions with high precision, but the result may have lower sensitivity than that obtainable using a CNN. Accordingly, ROIs identified by the object detector may be marked as high probability and those identified by the CNN (e.g., with a reduced threshold to enhance sensitivity) may be marked as lower probability. This approach may be advantageously used to prioritize medical images for review. For example, a collection of mammograms, or the individual images in a multi-image 3D mammogram, may be ranked in terms of priority by the number of high-precision pixels, or by a weighted sum of high-precision and high-recall pixels, in each image.

While object-detection algorithms have proven themselves capable of distinguishing among clearly different object types, they may have more difficulty distinguishing among tissue types whose differences are subtle, or where an image has limited information content. For example, chest X-rays may reveal one or more of numerous conditions such as atelectasis, consolidation, pleural effusion, pulmonary fibrosis, aortic enlargement, cardiomegaly, etc. These conditions may share various visual similarities in an X-ray image, which is not only grayscale but may have limited resolution or imaging sensitivity. Similarly, mammograms may contain potentially malignant masses that are difficult to distinguish visually, given limited resolution and the absence of color, from fibrous breast tissue. In such cases, it may be useful to apply an ensemble of object-detection algorithms and combine the resulting predictions using a combination technique such as weighted boxes fusion, soft nms, or other suitable technique.

The probability map may be color-coded, with different colors assigned to discrete probability ranges. For example, the color coding may follow the visible spectrum, with low probabilities corresponding to blue and high probabilities represented by red, and intermediate probability ranges assigned to intermediate spectral colors. The number of colors used (i.e., how finely the probability range of 0 to 1 is partitioned) depends on the classification task and how meaningful small probability gradations are for the viewer. Alternatively or in addition, regions may be colored to indicate sensitivity vs. precision or specificity. In some embodiments, high-specificity regions (e.g., identified by an object detector) are marked red while high-sensitivity regions (e.g., identified by CNN 135) are marked yellow. The high-specificity regions tend to surround target abnormalities tightly; the high-sensitivity regions may be more diffuse and occupy more of the image, but will capture ROIs that may be absent from the high-specificity regions. The color marking may be in the form of an overlay or contour boundary surrounding a ROI.

The classification need not be binary. For example, CNN 135 may be trained with subimages 128 corresponding to three types of tissue, e.g., normal tissue and two distinct types of malignant tumor. For example, in colorectal cancer, subtypes include high and low microsatellite instability, which may be differentiated computationally as described in Frank, "Accurate diagnostic tissue segmentation and concurrent disease subtyping with small datasets," *J. Path.*

*Inform.*, 14:100174 (2023), https://doi.org/10.1016/j.jpi.2022.100174, the entire disclosure of which is hereby incorporated by reference. As used herein, the term "subtype" can also connote the severity of a condition or other characteristic or refinement of the analyzed tissue. For example, the Gleason score is typically used to grade the severity of prostate cancer. Instead of binary classification into tumor and nontumor regions, probabilities may be computed according to, for example, a softmax activation function corresponding to different subtypes. Pixel-level probabilities from overlapping tiles can be averaged as described above or, because the softmax function is a ratio of exponentials, the mean may be weighted or otherwise adjusted. More simply, the softmax probabilities associated with each pixel may be summed and the class label corresponding to the largest sum (identified, for example, using the argmax( ) function to select a label index) assigned to the pixel with, e.g., a probability of 1. Following these assignments, classification map 145 will have pixels with class labels corresponding to the highest softmax probability. A dataset such as the publicly available PANDA dataset (see Bulten et al., "Artificial intelligence for diagnosis and Gleason grading of prostate cancer: the PANDA challenge," *Nat. Med.* 28, 154-163 (2022), https://doi.org/10.1038/s41591-021-01620-2) can be used to identify different Gleason regions for multiclass instead of binary training.

Figure 3:
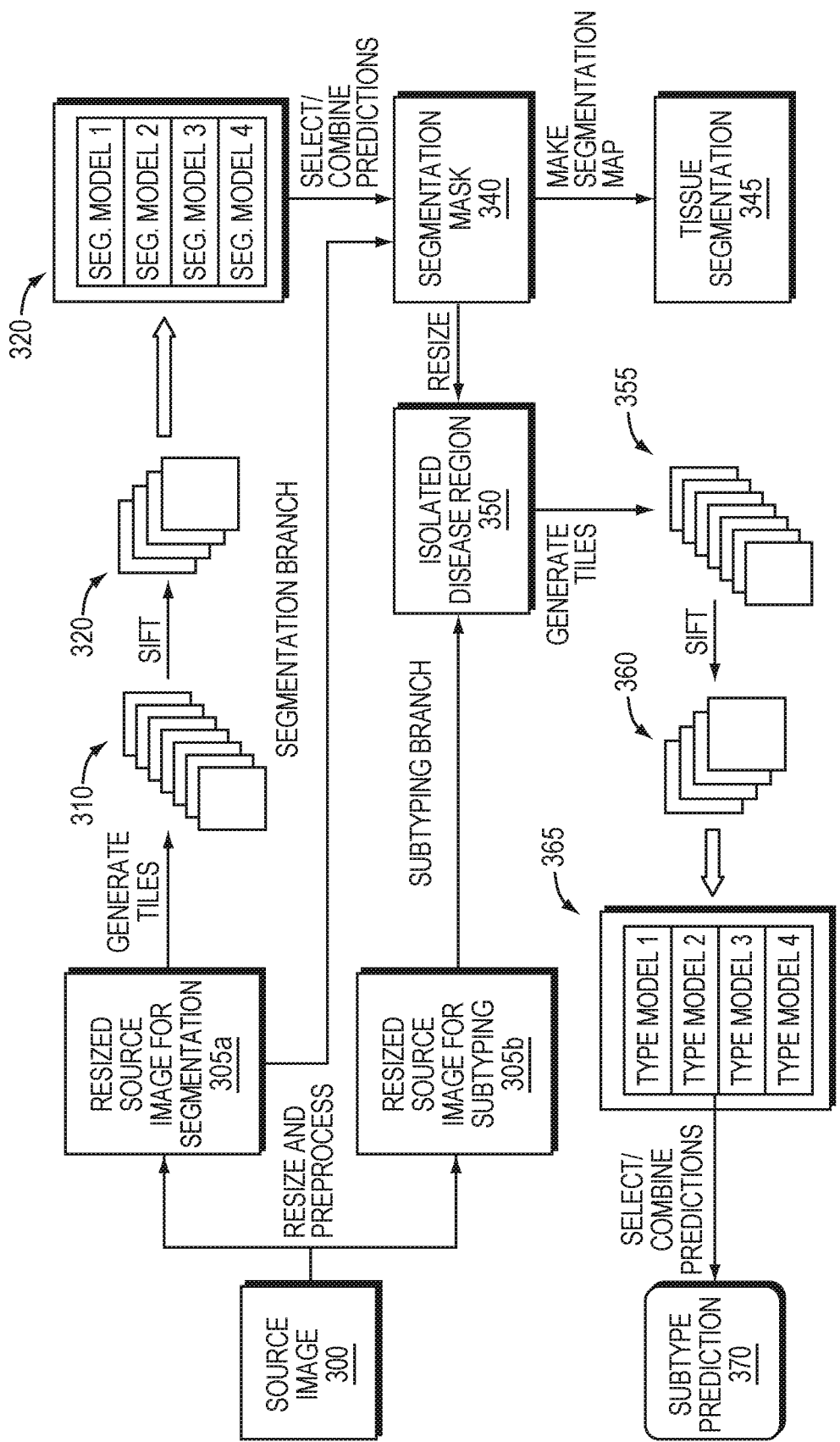
FIG. 3 schematically depicts a workflow according to embodiments of the invention.

Alternatively, the tasks of segmentation and subtyping may be handled separately, e.g., as a sequence of binary classification tasks or applying a softmax function to regions that have been identified, as described above, as abnormal. This approach separates the classification and subtyping tasks, which may be advantageous in terms of CNN accuracy or enabling use of more specialized subtyping. FIG. 3 illustrates concurrent segmentation and subtyping in accordance with embodiments of the invention. With reference to FIGS. 1 and 3, a source medical image 300 is resized to an optimal size 305*a* for segmentation and also to an optimal size 305*b* for subtyping. The images 305*a*, 305*b* may be stored in one or more image buffers of main memory 106. In the segmentation processing branch, tiles 310 are generated from the resized source image 305*a* in accordance with a specified overlap, and then optionally sifted by subimage analyzer 130 to produce a sifted tile set 320. For example, the tiles 310 may be sifted using entropy rails established for the type of medical image and tissue type under study. The sifted tiles 320 are presented to a plurality of predictors 330 that have been trained on different training sets as described above. In particular, the predictors 330 (indicated as Segmentation Models 1-4 in the figure, though there may be any suitable number of predictors) have been trained to distinguish between or among tissue types, e.g., between diseased and undiseased tissue.

Assuming for illustrative purposes that the tissue types are diseased and undiseased (e.g., tumor and non-tumor) tissue, each of the predictors 330 analyzes each of the tiles and produces a prediction (e.g., a probability) whether the tile is diseased or undiseased. The prediction probabilities are selected or combined as discussed in detail below to produce a single prediction classifying the tile. Once all of the tiles 320 have been classified, the classifications are used to produce a binary segmentation mask 340. The regions corresponding to tiles classified as diseased tissue, for example, can simply be combined in a union operation to form the white or transparent portion of the mask 340, or pixel-level classification probabilities can be derived from the union of tiles as described above, with pixels classified as diseased forming the white or transparent mask portion.

The mask 340 may be applied to the resized source image 305*a* to produce a tissue segmentation 345. For example, regions of the source image 305*a* corresponding to the white or transparent portion of the mask 340 may be highlighted, colored, or otherwise distinguished from the rest of the image 305*a* in the tissue segmentation 345. As explained below, segmentation mask 340 may alternatively be produced using an object detector or, for small images, a CNN (having, for example, a U-Net architecture) that analyzes the entire image and produces a segmentation directly.

In the subtyping branch, the segmentation mask 340 is resized as necessary to conform dimensionally to the resized source image 305*b*, and is then applied to the source image 305*b* to occlude all regions thereof that have been classified as undiseased. Tiles 355 are generated from the isolated disease region 350 at a desired degree of overlap. These may be sifted to exclude tiles with too much background, but since the disease region 350 has been defined based on tiles that have already been classified, sifting may be minimal or omitted entirely. The sifted tiles 360 are applied to one or more predictors 365 (e.g., Type Models 1-4) that have been training to distinguish among subtypes. For example, Type Models 104 may have been trained on different training sets. The output of the predictor 365, or the averaged predictions of multiple predictors 365, provide the subtype prediction 370.

It has been found that for some applications, the spread among predictions produced by predictors trained for the same classification task on different training sets may indicate a degree of uncertainty in the reliability of the prediction. For example, a prediction may have a high confidence level if the the difference between maximum and minimum prediction probability values (ranging from 0 to 1) is less than 0.25, or less than 0.2, or less than 0.15; whereas a spread exceeding 0.3, 0.4 or 0.5 may correspond to a low confidence level due to the greater uncertainty. The exact values depend on various factors including the size of the training sets and the nature of the classification task, but are straightforwardly determined empirically without undue experimentation.

For example, in the case of normal tissue and two or more distinct subtypes (e.g., Gleason grades) of malignant tumor, a first CNN 135 may be trained to discriminate between normal tissue and malignant tissue generally, and a second CNN 135 may be trained to discriminate among subtypes. A source image 122 may be decomposed into tiles that are sifted and presented to the first CNN 135, which identifies a set of tiles corresponding to tumor tissue. These tiles may be analyzed and used to create a probability map 148 as described above. In addition, they may be analyzed by the second CNN 135 to classify the tumor in terms of its subtype. For example, the classification probabilities generated by the second CNN 135 may be aggregated in a probability framework (e.g., averaged or weighted) to produce an overall subtype classification, or the pixel-level classification probabilities may instead be retained and used to modify probability map 148 to indicate the locations of the different subtypes (e.g., with different colors corresponding to different Gleason grades).

In particular, if the image to be analyzed is known to contain only one of multiple classifications, the dominant label among labeled pixels—that is, the label with the most pixel assignments—may be identified, and in some implementations, only pixels having that label are mapped in probability map 148. If the subimage size is small enough, the dominant label can be assessed at a subimage level, and the pixels of classification map 145 corresponding to those of each subimage classified with the dominant label are assigned a probability of 1. These pixels may be assigned a monochromatic color and translucently superimposed over the grayscale version of source image 122 (or used to form colored boundaries on the image) to generate the final probability map 148. Thus, in this case, combining class probabilities means assigning a value of 1 to any pixel intercepted by any number of tiles having the dominant label (and assigning a value of 0 otherwise).

If the image might validly have multiple classifications, on the other hand, these classifications may be mapped in different colors on a single probability map 148. Alternatively, multiple probability maps each colored to show one of the classifications may be generated. For example, CNN 135 may be trained to discriminate among multiple subtypes, but suppose it is known that any malignant histology sample can contain only one subtype. In that case, the image of a new sample may be tiled and sifted in accordance with a visual criterion, and the sifted tiles presented to CNN 135 for classification. Due to error, the resulting classifications may incorrectly include more than one tumor type. If CNN 135 has been properly trained, the correct classification type will predominate among tiles classified in one of the malignant categories (as opposed to classification as normal tissue). The minority tiles may therefore be ignored and only the dominant tumor tiles mapped. Since the minority tiles are excluded altogether rather than being averaged with the dominant tiles, there is no need for probability-based color coding; the dominant tiles may be overlaid in a single color on a grayscale version of the sample image, producing a tissue segmentation indicating the location and type of tumor in the sample—that is, the union of all dominant tiles will be colored monochromatically in probability map 148.

In some instances, the tile size corresponding to segmentation accuracy may differ from that producing best classification performance—e.g., segmentation accuracy favors smaller tile sizes for maximum resolution while the optimal tile size for classification may depend on the distribution of relevant tissue abnormalities within a diseased region. In such cases, segmentation may be performed first (using the first CNN 135) and used to create a binary mask, which is applied to the source image to isolate the predicted abnormal region(s). Tiles at the optimal classification size may be obtained from the isolated region, sifted, and analyzed using the second CNN 135 to classify the abnormal region. Moreover, tile characteristics other than size may be different for the classification and subtyping branches.

Tile characteristics other than (or in addition to) size may be different for the different branches so long as analysis is confined to the abnormal region 350. For example, the tile resolution may be different; in some embodiments, the source image 305b may be larger or small than the source image 305a, or may be obtained at a different magnification level. As a result, identically sized tiles will have different resolutions. Segmentation mask 340 may be resized to conform to source images 305a, 305b as appropriate.

More generally, any suitable approach to identifying subtypes in abnormal region 350 may be employed; that is, the subtyping branch need not use the tiling approach discussed above for subtyping. For example, once malignant regions of a prostate biopsy or resection have been identified, Gleason scores may be assigned in accordance with known computational techniques as described, for example, in Bulten et al., "Automated Gleason Grading of Prostate Biopsies using Deep Learning," arXiv:1907.07980v1 [ees-s.IV]18 Jul. 2019; Arvaniti et al., "Automated Gleason grading of prostate cancer tissue microarrays via deep learning," *Scientific Reports* 8:12054 (2018), DOI:10.1038/s41598-018-30535-1; and Mun et al., "Yet Another Automated Gleason Grading System (YAAGGS) by weakly supervised deep learning," *npj Digital Medicine* (2021) 99, the entire disclosures of which are hereby incorporated by reference. Gleason scores may be visualized with different colors. For example, once tumor regions are identified, Gleason grades 3 through 5 may be indicated by different colors applied to the identified tumor regions.

Alternatively or in addition, image entropy may be used to produce boundary constraints rather than a unitary criterion that either is or is not satisfied. This is particularly useful in creating tissue segmentations, which in this context refers to probability maps distinguishing between two or more different tissue types. Frequently, the distinction is between normal and abnormal (e.g., diseased) tissue. The tissue segmentation may take the form of a colored probability map or a binary mask that, e.g., is black for all normal tissue areas and white or transparent for all abnormal tissue regions. Such a mask is considered a probability map as the latter term is used herein. The segmentation may also take the form of the source image or grayscale version thereof with ROIs marked, e.g., with colored dots, boundary lines or other indicators. For example, an object detector may be trained to detect and distinguish between cancerous and normal cells. The centroids of the detected cells may be indicated by differently colored dots corresponding to cell type or disease status (e.g., diseased vs. normal). Alternatively, a similar result can be achieved by producing a segmentation of the image, or non-overlapping portions thereof, using a segmentation architecture such as U-Net or a fully convolutional neural network; these are well-suited to identifying sharply defined tissue structures such as cells. The segmentation model may be trained to detect different cell classes, or a single class including all cells that are classified using a trained classification architecture such as EfficientNet or ResNet. Different types of identified cells may be counted to obtain a measure of, e.g., tumor cellularity that is, the proportion of tumor cells in a tissue sample, which may have clinical significance.

In one implementation, training images are prepared using segmentation masks that occlude normal (e.g., non-tumor) portions of an image. These masks may be generated manually, by trained experts, or in an automated fashion. The masks allow the abnormal (e.g., tumor) portions of a slide image to be extracted, and the resulting tumor-only images may be downsampled as described above and their image entropies computed. The maximum and minimum entropies of the images (or, if desired, of tiles created from the images) may be treated as boundaries or "rails" within which a candidate tile must fall in order to qualify as usable. Sifting in accordance with this criterion preliminarily eliminates tiles unlikely to correspond to tumor tissue. Thus, an image of a histology slide to be classified and/or mapped may be downsampled, tiled, and the tiles sifted using the previously established entropy boundaries. The remaining tiles may then be analyzed by CNN 135.

If the CNN has been trained to distinguish between normal and abnormal tissue as a binary classification, the entropy rails serve as a preprocessing check to exclude normal tissue tiles that might have been misclassified as tumor tiles. The tiles having the classification of interest (e.g., abnormal) may be mapped as discussed above; the union of all such tiles, as mapped, constitutes the tissue segmentation, which may be overlaid onto the original image or may instead be output as a binary mask. For example, in a binary classification, the union of all abnormal tissue tiles may overlaid onto the original image as white or transparent, with the remainder of the image rendered as black. Whether white/transparent or colored, the union of overlapping tiles represents an approximation of the abnormal tissue region—i.e., a tissue segmentation. The classification probabilities for overlapping tiles may, in some embodiments, be combined at a pixel level as described above. But in other embodiments, a simple union operation over all appropriately classified tiles is employed.

Due to the tile geometry, the segmentation region will have stepped edges that appear jagged. The edges may be smoothed with a median or other smoothing filter. (It should be noted that smoothing may be applied to any type of probability map described herein.) Furthermore, tile size limits the contour accuracy of the probability map; the larger the tile size, the more the edges of the map will spill over into the oppositely classified tissue region (e.g., into normal tissue). From a clinical perspective such over inclusiveness is perhaps to be preferred to the alternative, but in any case, the tile size is generally dictated by what works best for the overall task of classifying tissue. To compensate for this spillover effect, it is possible to apply isomorphic shrinkage to the mapped regions; the larger the tile size, the greater the degree of shrinkage that may be applied before or after smoothing. The optimal amount of image resizing for a given tile size is straightforwardly obtained without undue experimentation.

If CNN 135 has been trained to distinguish between normal and multiple types of abnormal tissue, the probability map may be based on the dominant abnormal tissue type as described above, i.e., the minority tiles may be ignored and only the dominant tiles mapped. Alternatively, all tiles classified as either type of abnormal tissue may be mapped (e.g., tiles corresponding to both the dominant and minority abnormal tissue types). The latter approach may be preferred if abnormal tissue tiles are more likely to be misclassified as the wrong type of abnormal tissue than as normal tissue.

Although the above discussion has focused on analysis of 2D images, the same approaches can be used for 3D images. Tomographic images, for example, represent a 3D volume as a series of sectional 2D slices. Most simply, the foregoing techniques can be applied individually to 2D tomographic slices, which may be reviewed serially and, if desired, ranked according to the amount of abnormal tissue detected. Tomographic and similar imaging modalities can also be used to create fully 3D images of anatomic features; thus, while 3D mammograms (or "tomosyntheses") consist of slices, a 3D image is a solid volume that may be rotated and translated onscreen in three apparent dimensions. For example, a series of low-dose X-ray projections may be acquired in a circular trajectory around a patient's breast, followed by computed tomography (CT) image reconstruction to provide a 3D breast volume. (See, e.g., O'Connell et al., "The potential role of dedicated 3D breast CT as a diagnostic tool: Review and early clinical examples," *Breast J.* 2014 November; 20(6): 592-605, incorporated herein by reference.) The imaged volume is typically represented by volumetric pixels ("voxels") defined by the tomographic reconstruction. The foregoing techniques may be applied to a 3D voxel image by defining 2D slices through the 3D image and analyzing each slice as discussed above. These slices can be taken along any desired axis, or along more than one axis. The slices may correspond to adjacent 2D layers, or the 2D layers may be spaced apart. For example, if the voxel dimension (in $mm^3$) is d, but the smallest diagnostic feature of interest can be no smaller than 3d, it is safe to extract and analyze every third 2D layer along the axis of interest for diagnostic purposes. On the other hand, by analyzing substantially all 2D layers along an axis, the 3D tomographic reconstruction can be augmented to highlight detected ROIs in three dimensions; for example, voxels lying within detected regions may be labeled and rendered in accordance with the labels. As described above, embodiments of the invention may be used to detect high-precision and high-recall ROIs, which may be colored or otherwise marked in the 3D reconstruction. As is known in the art, the 3D reconstruction may be viewed as a solid image that can be sliced arbitrarily, showing sectional anatomic detail, or as a partially transparent 3D image in which only certain features are rendered within the depicted volume. In the latter case, high-precision and high-recall ROIs may be shown as, for example, red and yellow volumes within, e.g., an otherwise transparent contour outline of the breast. If efficiency considerations preclude analysis of all 2D layers within a volume of interest, layers can be skipped and the omitted regions filled by interpolation so long as the analyzed layers are close enough together to avoid the possibility of missing diagnostically relevant features.

Figure 4:
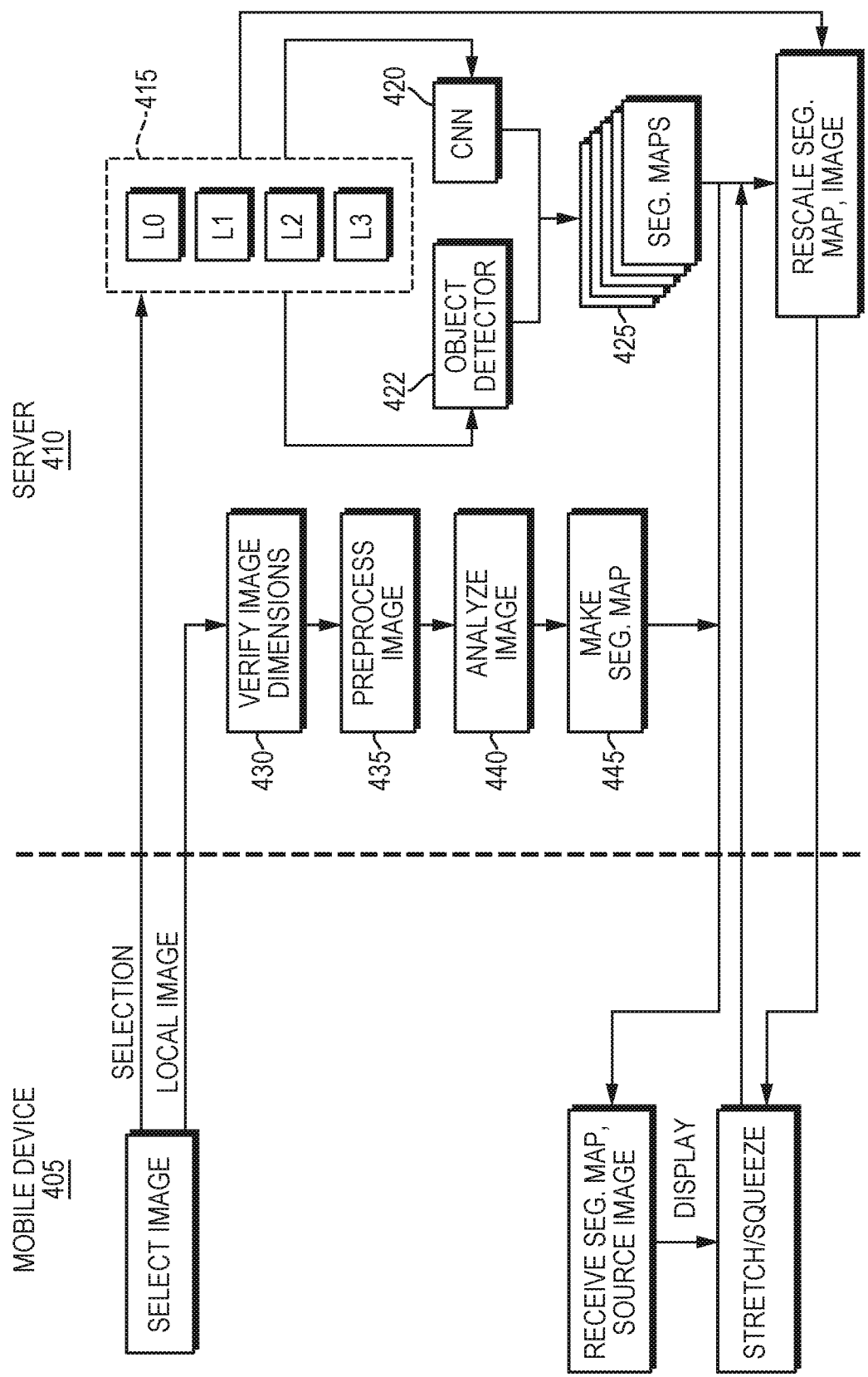
FIG. 4 is a workflow diagram schematically depicting a representative division of functionality between a mobile device and a server.

With reference to FIG. 4, the functionality described above may be shared between a mobile device 405 and a conventional server 410, which may be in communication over a network via a conventional network interface; for example, server 410 may be a web server and the network may be the Internet or the public telecommunication infrastructure. The user first selects a medical image on mobile device 405. The medical image may be stored locally on mobile device 405 and uploaded to server 410, or may instead be resident on server 410, in which case the user taps a screen feature (e.g., an image thumbnail) and the user's selection is transmitted to server 410. The selected medical image may be a whole-slide image, an X-ray, a tomographic image, a mammogram, or other digital representation of an internal and/or external anatomic region or a slide (e.g., a biopsy slide).

A source image 415 may be stored on server 410 at a plurality of resolutions (e.g., as images of different sizes or, as described above, as sets of tiles having different zoom resolutions). As used herein, the expression "stored on" or "stored at" a server is not limited to storage on the particular hardware element implementing the server functionality; instead, images may be stored in a storage area network or on other servers (i.e., in the cloud) or devices, and so long as the stored images are available to the server 410, they are considered stored thereon regardless of the physical locations of the files. In some cases, a single discrete file holds multiple versions of the same image at different resolutions. For example, TIFF is a tag-based file format for storing and interchanging images. A TIFF file can hold multiple images in a single file. The term "Pyramid TIFF" refers to a TIFF file that wraps a sequence of bitmaps each representing the same image at increasingly coarse spatial resolutions. The individual images may be compressed or tiled. Similarly, SVS files are multi-page TIFF files that store a pyramid of smaller TIFF files of an original image. The different resolutions are related in terms of pixel count and downsample factor, and for medical images obtained using microscopy, a magnification factor. Data characterizing a representative set of multilevel files, each containing the same image at different resolutions, is set forth in Table 1.

TABLE 1

| Level | Average Dimensions (pixels) | Downsample Factor | Magnification |
|---|---|---|---|
| L0 | 116,214 × 88,094 | 1 | 40× |
| L1 | 29,053 × 22,023 | 4 | 10× |
| L2 | 7263 × 5505 | 16 | 2.5× |
| L3 | 3498 × 2662 | 32 | 1.25× |

The optimal level to use for segmentation analysis depends on the application. Some diseases manifest in large enough regions of, for example, a biopsy slide that even a relatively coarse resolution (e.g., L3) is sufficient for analysis; the image may be tiled as described above and analyzed by a CNN 420 trained on similarly sized tiles drawn from images of similar or identical resolution; alternatively or in addition, a still coarser version of source image 415 may be analyzed in whole by an object detector 422 trained on similarly sized images. In other embodiments, source image 415 is stored as separate files, each at a different resolution, in an image library.

The output of CNN 420 or object detector 422 may be used as (or to generate) a tissue segmentation map 425 at the resolution of the analyzed image. The segmentation map may be scaled to the other stored resolutions and, if desired, to intermediate resolutions; that is, it need not be stored at multiple resolutions. For example, a binary mask or color overlay may simply be scaled geometrically; enlargement results in no meaningful loss of resolution because the mask or overlay regions are graphic entities rather than image data. These elements may be stored separately or applied to the differently scaled source images, in native or grayscale format, and the resulting mapped images stored separately as indicated in FIG. 4. The latter approach requires more server storage but enables rapid access to differently scaled images as the user of mobile device 405 stretches or squeezes the viewed image. The former approach involves creating differently scaled segmentations on the fly, which may be preferred for large images, particularly if the user is not expected to dramatically and frequently stretch or squeeze the images so as to traverse multiple image scales.

Server 410 may implement the functionality described above in connection with system 100. Hence, server 410 may process an incoming image from mobile device 405 by initially verifying that the image resolution corresponds to the resolution of images on which CNN 420 was trained (step 430), and adjusting the resolution as necessary. Server 410 may then perform various conventional preprocessing tasks such as equalization, contrast adjustment, cropping, removal of spurious or patient-identifying markings, stain normalization, etc. (step 435). Server 410 thereupon generates and sifts tiles from the selected image, analyzes them using CNN 420 (step 440), and generates a tissue segmentation map as described earlier (step 445); for example, the tissue segmentation map may highlight ROIs in different colors corresponding to probability levels of an abnormality. Alternatively or in addition, the received image may be analyzed (e.g., at a lower resolution following downscaling) by object detector 422. In the absence of previously stored images 415 corresponding to the received local image at different resolutions, server 410 is limited in terms of the additional image data it can supply as the user of mobile device 405 stretches the local image (which is, in this case, the highest-resolution image available to server 410). But server 410 can still perform the analytical and segmentation steps 430-445 that may otherwise be too computationally intensive for practical execution on mobile device 405. As noted previously, although the foregoing discussion assumes that server 410 performs the depicted operations, they may be performed on one or more other computational devices in communication with server 410. For example, the preprocessing, analysis and mapping tasks 430-445 may be performed by one or more other servers or computers in communication with server 410.

The segmentation map may take various forms, as noted—e.g., it may have the same dimensions as the selected image, it may be a grayscale or color image with an overlay reflecting different probability levels, and it may be represented as an image (such as a bitmap or compressed—e.g., .jpg or .png—image) or as rendering instructions for producing a graphic overlay (e.g., a color probability map with filled or outlined regions). The segmentation map may be provided to mobile device 405 directly, via a network connection, a download link or other indirect means. If the source image was originally present on server 410 rather than mobile device 405, the source image may be provided to mobile device 405 along with the segmentation map at a resolution appropriate to convenient download and initial display.

The mobile device 405 is configured to permit the user to toggle between the selected image and the received tissue segmentation map. Mobile device 405 may allow the user to gesturally control image magnification (e.g., using pinch and stretch gestures) and toggle between substantially identically magnified versions of the source image and the tissue segmentation map. In this way, for example, the user may zoom in on a colored ROI and then toggle to the source image to inspect the anatomy more closely. This toggling function is straightforwardly implemented using, for example, dual image buffers and a conventional mobile application that acquires and applies the coordinates of a first displayed image to another image that replaces it. Alternatively, as noted, the segmentation map may be an overlay applied to the source image and defined in vectorized or geometric form (rather than as an image bitmap), or may even simply be rendering instructions for a filled or border overlay. Toggling between the source image and the segmentation map, therefore, may be no more than a trigger for applying the overlay to, or removing it from, the displayed source image (or a grayscale version thereof). Functionality for viewing the image on mobile device 405 may be implemented locally, as an installed application, or as a web application in communication with server 410 (e.g., with background downloading of scaled image tiles as the user pans or zooms for fast toggling).

When the user stretches the displayed image, the resolution becomes coarser. To enable the user to see more detail, the coordinates of the displayed image portion are sent to the server following the user's stretch gesture. Based on these image coordinates, server 410 selects a higher-resolution version of the source image and corresponding segmentation map and, based on the mapping among stored images, sends higher-resolution content for display on mobile device 405. This may be implemented in various ways. In one embodiment, as noted earlier, source image 415 and corresponding segmentation maps 425 are stored at multiple resolutions, e.g., L0-L3 shown in FIG. 4. The image initially passed to mobile device 405 may be, for example, the L3 version. Server 410 establishes a mapping between the images at different resolutions. The mappings may be geometric or coordinate transformations such as linear or affine transformations, enabling coordinates in one image to be mapped to corresponding coordinates in one or more other images. The server 410 may rescale the tissue segmentation image 425 that it generates, or may select from among previously generated images at different rescalings, before transmitting an image and its associated segmentation map to mobile device 405. The mappings among images may be stored as transformation matrices reflecting two-dimensional enlargement or contraction of all distances in a particular direction by a constant factor. For example, the mappings may be pairwise mappings between successive resolution levels. The image storage and mapping may precede interaction with and provision of image data to mobile devices.

In another embodiment, zooming is implemented using a tiled web map. Often used to support geographic maps, tiled web maps divide a map or other image into tiles of, e.g., 256×256 pixels. A series of discrete zoom levels is defined, each zoom level corresponding to a set of tiles collectively representing the source map or image. At the outermost zoom level, the entire map or image may be represented in a single low-resolution tile. Each zoom level doubles the number of tiles in both dimensions, so that the single tile is replaced by four tiles (2×2) at the next zoom level—that is, at this zoom level, the entire map or image is represented by four 256×256-pixel tiles, each having a higher resolution than the tiles of the preceding zoom level. At the next zoom level the map or image is represented by 16 (4×4) tiles, at the next zoom level by 64 (8×8) tiles, and so on. There may be a few or dozens of zoom levels, depending on the desired zoom range. This approach is efficient mechanically since the tiles at all zoom levels can be cached and selectively supplied by server 410 to a user's display device based on the portion of the image to which the user has zoomed. As the user pans, most of the tiles are still relevant, and can be kept displayed, while new tiles are fetched from server 410. See, e.g., Wikipedia, "Tiled Web Map," available at https://en.wikipedia.org/wiki/Tiled_web_map, and references cited therein.

When the user of the mobile device 405 changes the magnification of the viewed lower-resolution image (e.g., gesturally, as noted above), the coordinates of the currently displayed image portion may be transmitted to server 410, which uses the mapping to identify the corresponding portion of the image (or tiles corresponding thereto) represented at a higher resolution but, again, depicting substantially the same subject matter. Server 410 thereupon returns this image portion (or tiles) to mobile device 405. Conventional image-handling functionality on mobile device 405 causes this image portion to replace the displayed lower-resolution image portion, affording the user access to more anatomic detail. To the user stretching an image to examine a point of detail, the enlarged image appears to come into better focus as the coarser subject matter is replaced by more highly detailed image data. If the user continues to stretch the image, corresponding subject matter from progressively higher-resolution image versions may be identified and transmitted to mobile device 405 for display thereon. As a result, the user is able to examine detail up to the resolution limit of the highest-resolution image stored on server 410.

The image-handling functionality on mobile device 405 may trim, resize or resample the received image portion so that it smoothly replaces its lower-resolution counterpart on the display; for example, the user may stop stretching the image at a magnification level intermediate between server-stored levels, so the image-handling functionality may resize the received image portion so it displays properly.

In some embodiments, replacement of the lower-resolution displayed image with the higher-resolution fragment thereof occurs upon user command. For example, an application executing as a running process on mobile device 405 (an "app") may present a button graphic which, when tapped, causes transmission of image coordinates to server 410, which responsively retrieves and makes available (e.g., transmits) to mobile device 405 the corresponding fragment of the higher-resolution image. Tapping again may cause the app to replace the displayed higher-resolution fragment with the congruent portion of the lower-resolution image, enabling the user to once again stretch or squeeze the displayed image. Alternatively, the app may sense a stretch operation and, in response, automatically transmit image coordinates of the displayed image portion to server 410, which responsively retrieves and makes available to mobile device 405 the corresponding fragment of the higher-resolution image, which is then displayed. Because only a portion of the high-resolution image has been buffered on the mobile device, the user can stretch but not significantly shrink the high-resolution image. Hence, when the app detects a pinch gesture on the device touchscreen that would require display of unavailable image data, it may replace the displayed higher-resolution fragment with the congruent portion of the lower-resolution image before shrinking the image (and displaying more of it) in response to the pinch gesture. Alternatively, the lower-resolution image data may be cached on mobile device 405. In still other embodiments, full images at multiple resolutions (e.g., two adjacent images and associated segmentation maps) and mappings (e.g., transformation matrices) therebetween, or tiles representing different image resolutions, may be downloaded to and cached on mobile device 405, enabling fast response to gestural changes in image magnification. Alternatively, a reduced image may created on mobile device 305 simply by downscaling the displayed image in real time in response to a pinch gesture. In web app embodiments, more functionality resides on server 410, although the current image or portion thereof may be cached on mobile device 405 so that user pans and zooms are executed instantly.

Mobile device 405 may also include annotation capability, enabling the user to mark the displayed image. It is conventional, for example, for mobile devices to support touch-based annotation which, when activated, records the pixels touched by the user as she moves her finger against the display. In this way, the user may draw a circle or other shape around a displayed feature, and the shape appears on the display in a predetermined or selected color. The annotated image can be saved or shared via email, instant messaging, or other means.

This approach may be less than ideal for medical images containing small but critical features. Accordingly, in various embodiments, mobile device 405 is programmed the sense stationary contact between the user's finger and the touchscreen and, after a short delay to confirm the user's intent, draws a circle or other shape that expands outwardly from the region of contact. Once contact is no longer sensed, the shape stops expanding but remains in place. In this way, the user may simply touch a feature of interest, watch the shape expand, and remove his finger when the shape is large enough to enclose the feature. The user may also be permitted to select the line thickness and color of the shape, or may select a filled shape that, for example, translucently covers the region of interest instead of surrounding it. In still other embodiments, artificial intelligence or computer vision (CV) techniques are used to infer the contour(s) of the feature of interest and conform the shape to this feature. Suitable CV algorithms for this purpose include the Harris feature detector, SIFT (scale-invariant feature transform), SURF (speeded-up robust feature), FAST (features from accelerated segment test), BRIEF (binary robust independent elementary features), ORB (oriented FAST and rotated BRIEF), and BRISK (binary robust invariant scalable keypoints).

The annotation procedure may be repeated for multiple features in an image. The user may also be permitted to erase any or all drawn shapes and, if desired, draw them again with the same or a different marking approach (e.g., fill rather than outline).

It should be understood that the term "network" is herein used broadly to connote wired or, more typically, wireless networks of computers or telecommunications devices (such as wired or wireless telephones, tablets, etc.). For example, a computer network may be a local area network (LAN) or a wide area network (WAN). When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Networked computers may be connected over the Internet, an Intranet, Extranet, Ethernet, or any other system that provides communications. Some suitable communications protocols include TCP/IP, UDP, or OSI, for example. For wireless communications, communications protocols may include IEEE 802.11x ("Wi-Fi"), BLUETOOTH, ZIGBEE, IRDA, near-field communication (NFC), or other suitable protocol. Furthermore, components of the system may communicate through a combination of wired or wireless paths, and communication may involve both computer and telecommunications networks. For example, a user may establish communication with a server using a "smart phone" via a cellular carrier's network (e.g., authenticating herself to the server by voice recognition over a voice channel); alternatively, she may use the same smart phone to authenticate to the same server via the Internet, using TCP/IP over the carrier's switch network or via Wi-Fi and a computer network connected to the Internet.

In general, it is noted that computers (such as system 100 and server 305) typically include a variety of computer-readable media that can form part of system memory and be read by the processing unit. By way of example, and not limitation, computer-readable media may take the form of volatile and/or nonvolatile memory such as read-only memory (ROM) and random access memory (RAM). A basic input/output system (BIOS), containing the basic routines that help to transfer information between elements, such as during start-up, is part of operating system 120 and is typically stored in ROM. RAM typically contains data and/or program modules that are immediately accessible to and/or presently being operated on by a CPU (e.g., CPU 108). An operating system may be or include a variety of operating systems such as Microsoft WINDOWS operating system, the Unix operating system, the LINUX operating system, the MACINTOSH operating system, the APACHE operating system, or another operating system platform.

Any suitable programming language may be used to implement without undue experimentation the analytical, communication and data-handling functions described above. Illustratively, the programming language used may include without limitation, high-level languages such as C, C++, C#, Java, Python, Ruby, Scala, and Lua, utilizing, without limitation, any suitable frameworks and libraries such as TensorFlow, Keras, PyTorch, or Theano. Further, it is not necessary that a single type of instruction or programming language be utilized in conjunction with the operation of the system and method of the invention. Rather, any number of different programming languages may be utilized as is necessary or desirable. Additionally, the software can be implemented in an assembly language and/or machine language.

CPU 108 may be a general-purpose processor, e.g., an INTEL CORE i9 processor, but may include or utilize any of a wide variety of other technologies including special-purpose hardware, such as GPU 110 (e.g., an NVIDIA 2070), a microcontroller, peripheral integrated circuit element, a CSIC (customer-specific integrated circuit), ASIC (application-specific integrated circuit), a logic circuit, a digital signal processor, a programmable logic device such as an FPGA (field-programmable gate array), PLD (programmable logic device), PLA (programmable logic array), smart chip, or any other device or arrangement of devices that is capable of implementing the steps of the processes of the invention.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

The invention claimed is:

1. A method of computationally representing and displaying a digital tissue segmentation image and a source digital image, the method comprising the steps of:
computationally generating, from a source digital image of an anatomic region, a digital tissue segmentation image visually indicating regions of interest corresponding to a physiologic condition associated with at least portions of the anatomic region;
alternately displaying each of the source digital image and the digital tissue segmentation image or corresponding portions thereof in registration at a first gesturally selected magnification level; and
responsive to a gestural selection of a second magnification level higher than the first magnification level, alternately displaying each of the source digital image and the digital tissue segmentation image or corresponding portions thereof in registration at the second gesturally selected magnification level.

2. The method of claim 1, wherein the digital tissue segmentation image designates, and colorwise distinguishes, high-precision regions of interest and high-recall regions of interest superimposed on corresponding regions of the the source digital image.

3. The method of claim 1, wherein the digital tissue segmentation image is an overlay.

4. The method of claim 1, wherein the source digital image and the digital tissue segmentation image have substantially identical dimensions.

5. The method of claim 1, further comprising computationally analyzing one or more of the regions of interest to identify the physiologic condition.

6. The method of claim 5, further comprising computationally analyzing one or more of the regions of interest to identify a subtype associated therewith.

7. The method of claim 6, wherein the subtype is a cancer subtype.

8. The method of claim 6, wherein the subtype is a cancer severity level.

9. The method of claim 1, wherein the digital tissue segmentation image is computationally generated at least in part by:
- computationally generating a plurality of overlapping subimage regions of the source digital image;
- computationally analyzing at least some of the subimage regions using a predictor to produce classification probabilities therefor;
- computationally combining, for each pixel of the source image contained within a plurality of subimage regions, the classification probabilities corresponding to all of the analyzed subimage regions containing the pixel; and
- computationally generating the digital tissue segmentation image based at least in part on the pixelwise combined predictions.

10. The method of claim 1, wherein the digital tissue segmentation image is computationally generated at least in part using an object detector.

11. A system comprising:
- a remote computer configured to store and transmit a digital tissue segmentation image computationally generated from a source digital image of an anatomic region, the digital tissue segmentation image visually indicating regions of interest corresponding to a physiologic condition associated with at least portions of the anatomic region; and
- a local device configured to (i) receive the digital tissue segmentation image from the remote computer, (ii) alternately display each of the source digital image and the digital tissue segmentation image or corresponding portions thereof in registration at a first gesturally selected magnification level, (iii) receive a gestural selection of a second magnification level higher than the first magnification level, and (iv) alternately display each of the source digital image and the digital tissue segmentation image or corresponding portions thereof in registration at the second gesturally selected magnification level.

12. The system of claim 11, wherein the digital tissue segmentation image designates, and colorwise distinguishes, high-precision regions of interest and high-recall regions of interest superimposed on corresponding regions of the the source digital image.

13. The system of claim 11, wherein the digital tissue segmentation image is an overlay.

14. The system of claim 11, wherein the source digital image and the digital tissue segmentation image have substantially identical dimensions.

15. The system of claim 11, wherein the remote computer is configured to generate the digital tissue segmentation image and computationally analyze one or more of the regions of interest to identify the physiologic condition.

16. The system of claim 15, wherein the remote computer is further configured to computationally analyze one or more of the regions of interest to identify a subtype associated therewith.

17. The system of claim 16, wherein the subtype is a cancer subtype.

18. The system of claim 16, wherein the subtype is a cancer severity level.

19. The system of claim 11, wherein the remote computer is configured to computationally generate the digital tissue segmentation image at least in part by:
- computationally generating a plurality of overlapping subimage regions of the source digital image;
- computationally analyzing at least some of the subimage regions using a predictor to produce classification probabilities therefor;
- computationally combining, for each pixel of the source digital image contained within a plurality of subimage regions, the classification probabilities corresponding to all of the analyzed subimage regions containing the pixel; and
- computationally generating the digital tissue segmentation image based at least in part on the pixelwise combined predictions.

20. The system of claim 11, wherein the remote computer is configured to computationally generate the digital tissue segmentation image at least in part using an object detector.

* * * * *